United States Patent
Nahum et al.

(10) Patent No.: US 10,269,446 B2
(45) Date of Patent: Apr. 23, 2019

(54) SYSTEM AND METHOD FOR REAL TIME DISPLAY OF DIAGNOSTIC LABORATORY DATA

(71) Applicant: Bio-Rad Laboratories (Israel) Inc., Rishon LeZion (IL)

(72) Inventors: Guy Nahum, Rishon Le Zion (IL); Shachaf Sagi, Rishon Le Zion (IL); Tal Segal, Nes Ziona (IL)

(73) Assignee: Bio-Rad Laboratories (Israel) Inc., Rishon-Lezion (IL)

( * ) Notice: Subject to any disclaimer, the term of this patent is extended or adjusted under 35 U.S.C. 154(b) by 43 days.

(21) Appl. No.: 14/284,404

(22) Filed: May 22, 2014

(65) Prior Publication Data
US 2015/0339354 A1  Nov. 26, 2015

(51) Int. Cl.
G06F 17/30 (2006.01)
G16H 10/60 (2018.01)
G06F 19/00 (2018.01)

(52) U.S. Cl.
CPC ............. G16H 10/60 (2018.01); G06F 19/00 (2013.01)

(58) Field of Classification Search
CPC .............. G06F 17/30554; G06F 17/30; G06F 17/30864; G06F 19/3418; G06F 19/3406; G06F 19/327; G06F 19/345; G06F 19/321; G06F 19/3487; G06F 19/3468; G06F 19/3481; G06F 19/3443; G06F 19/3462; G06F 19/3431; G06F 11/1464; G06F 17/3089; G06F 11/3485; G06F 19/322; G06F 17/24; G06F 17/30345; G06F 17/30964; G06F 9/4443; G06F 17/30368; G06F 17/30867; G06F 19/325; G06F 17/30424; G06F 17/30991; G06F 3/0482; G06F 17/30979; G06F 17/30112; G06F 17/30899; G06F 17/30395; G06F 17/30769; G06F 17/30029; G06F 17/30572; G06F 17/30032; G06F 17/30041; G06F 17/30044; G06F 19/00; G06Q 10/10; G06Q 10/103; G06Q 50/22; G06Q 50/24; G16H 10/60; G16H 40/20; G16H 50/20
USPC ....................................................... 707/722
See application file for complete search history.

(56) References Cited

U.S. PATENT DOCUMENTS

| | | | |
|---|---|---|---|
| 2003/0153818 A1* | 8/2003 | Bocionek | A61B 5/411 600/300 |
| 2005/0038791 A1* | 2/2005 | Ven | H04L 67/1095 |
| 2007/0233524 A1* | 10/2007 | Alban | A61F 2/95 705/3 |
| 2008/0208806 A1* | 8/2008 | Dalfo | G06F 17/30899 |
| 2011/0265032 A1* | 10/2011 | Weir | G06F 3/04847 715/810 |
| 2013/0007069 A1* | 1/2013 | Chaliparambil | G06Q 50/22 707/803 |
| 2013/0024511 A1* | 1/2013 | Dunn | G06Q 10/10 709/204 |

(Continued)

*Primary Examiner* — Evan Aspinwall
(74) *Attorney, Agent, or Firm* — Fenwick & West LLP (57) ABSTRACT

A system and method for real time updating and displaying medical diagnostics data, wherein the information stored in databases comprising large amounts of sensitive data that is being updated frequently are provided herein. By using a batch table for data filtering and a snapshot table for data retrieval, the system's performance remains substantially predictable and stable regardless of the base tables' size.

20 Claims, 9 Drawing Sheets (56) References Cited

U.S. PATENT DOCUMENTS

| | | | |
|---|---|---|---|
| 2013/0282758 A1* | 10/2013 | Seitz .................... | G06F 9/5016 |
| | | | 707/770 |
| 2014/0184422 A1* | 7/2014 | Mensinger ........... | A61B 5/0004 |
| | | | 340/870.02 |
| 2015/0169827 A1* | 6/2015 | LaBorde ............... | G06F 19/322 |
| | | | 705/51 |
| 2015/0261852 A1* | 9/2015 | Self ................... | G06F 17/30991 |
| | | | 707/754 |

* cited by examiner

SYSTEM AND METHOD FOR REAL TIME DISPLAY OF DIAGNOSTIC LABORATORY DATA

FIELD OF THE INVENTION

The present invention relates to system for analysis and display of information related to medical diagnostic devices. In particular the invention relates to displaying relevant data which is constantly added and updated.

BACKGROUND OF THE INVENTION

In the field of medical diagnostics, medical instruments may utilize methods such as chromatography to analyze blood samples from patients. Each chromatographic analysis may result in more than 200 kilobyte data cluster. Typical medical diagnosis equipment may be used in a hospital or a clinic for over 20 years, and provide analysis results for up to about 6000 samples each day. Thus, huge amounts of data related to the performed medical diagnosis data are accumulated over time.

Unlike traditional databases common to software applications in other fields, medical diagnostics may comprise little or no redundant data which can be ignored or even deleted. Every data record may potentially contain information which may be critical to a correct diagnosis of a patient. More so, each of the data records may contain information pertaining to the condition of the medical instrument as a whole or its parts, the operators of the instrument or the like, information which may be relevant in the detection of machine or human related malfunctions in the diagnosis process.

With medical instrumentation, data records regarding new samples are constantly generated and updated in a database.

Client applications typically access the database to obtain a recent snapshot of the data, usually by defining a filter indicating relevant records and data portions. A paging mechanism is typically used to obtain the snapshot, so that it can be displayed to a user, typically a machine operator or a member of the medical staff.

Traditional paging, however, does not allow the snapshot to be updated without user intervention when new records join the database. The user is typically not made aware of the ongoing changes and additions taking place in a relatively large dataset. Thus, the display rarely represents an accurate filtered, sorted view of relevant events in real-time.

Client-side paging is not effective when it comes to dealing with very large databases (VLDBs). Handling paging at the business logic level is not effective because each client may require different filtering and sorting. With specific server-side paging, each paging component utilizes its own set of data, procedures and logic within the database. More so, frequent database updates may eventually result in excessive memory consumption.

SUMMARY OF THE INVENTION

Typical medical diagnostics databases consume large disk space: the number of data records increases rapidly, and each data record may be, and typically is large (for example and without limitation ~200 Kb or more per single record). Medical records are highly sensitive, and thus records may need to be maintained in the databases without compromising long-term data integrity. Medical equipment is typically robust and long-lasting, as medical diagnostic systems often have a life span of ~20 years, and monitor diagnostics data taken from thousands of samples per day. The data aggregated may comprise not only pure medical laboratory test results, but also information about the physician, the patient, the diagnostics device, the time of day or the like.

The system is configured to keep client views comprising medical diagnostics data records automatically updated in real time. Each client view is defined by data selection filters according to specified criteria. The system uses the data selection filters for arranging and sorting large medical diagnostic event databases according to the selected criteria. The system is further capable of analyzing incoming events according to existing filters, and updating client views with relevant incoming events at real time. Filters are used by the clients to sort and display the information according to their needs. For example, there could be a plurality of client classes such as:

1. Medical care givers, such as doctors, that may be interested in reviewing records of a specific patient. These may want to view the progress of a specific test type such as cholesterol level or glucose level over time, or view results of different tests associated with a specific patient. Such client may be interested to view and compare similar results from a related group of patients, for example to discover family trends, etc.
2. Medical researchers that may be interested in reviewing records of a group of patients and perform statistical analysis of these records.
3. Lab technicians entering records or performing laboratory tests.
4. Billing and administration personnel, reviewing or modifying billing information.
5. System administrators, reviewing the operation of the IT system and monitoring the information flow.
6. Service personnel, monitoring the physical integrity and test accuracy.

Within each client class, individual clients may have different needs or preferences.

A method for updating and displaying medical diagnostics data according to some embodiments of the present invention may include: generating by at least one data generator a data record and a data notification associated with the generated data record and inserting the generated data record to a database; and applying to the data notification at least one client filter associated with at least one client.

Upon determination that the data notification matches the client filter, the method may further include generating and submitting a database query to the database by a data provider. The database may provide to the data provider, in response to the query, a record set associated with an updated view including the generated data record. The data generator may submit to the at least one client data objects associated with the record set. The at least one client may display the updated view comprising information derived from the record set.

In some embodiments of the present invention, the applying of the at least one client filter is performed by the data provider. In other embodiments, the applying of a client filter is performed by the at least one client, the applying further includes: submitting the data notification, by the data provider to the at least one client; applying to the data notification by the at least one client a respective filter associated with the at least one client. In such cases, the generating of a database query may include, upon determination that the data notification matches the client filter, generating and submitting a page request by the at least one client to the data provider; and generating by the data provider a database query associated with the page request.

According to some embodiments of the present invention, the at least one client may be one of a plurality of clients, and/or the at least one data generator may be one of a plurality of data generators.

It is another aspect of the current invention to provide a method of fetching, navigating within, and displaying a part of large medical diagnostics dataset, the method may include creating a list of results, which may include: receiving from a client, by a data provider at a server, selected search criteria; submitting the search criteria to a Data Access Layer (DAL); converting by the DAL the search criteria to database type search criteria and sending the database type search criteria to a database; and creating a list of matching results in a temporary table in the database and returning a list identifier of the list to the client.

Further, the method may include navigating over the list of results, which may include: receiving, by a data provider at a server, a page request including a list identifier of the created list and a page range; submitting the page request to the DAL; converting by the DAL the page request to a database type page request and sending the database type page request to the database; creating a page size list of results matching the page request and returning the page size list of results to the client; and displaying the page size list of results.

In some embodiments of a method according to embodiments of the present invention, the selected search criteria may include a selected filter and selected sort criteria. The creating of a list of results may be repeated, for example, by receiving from a client, by a data provider at a server, different selected search criteria, comprising the selected filter and different sort criteria. The navigating over a list of results may be repeated, for example, by receiving, by a data provider at a server, a page request including a list identifier of the created list and a different page range.

Although demonstrated herein through a specific example of medical diagnostics data, the system is generic and can be applied to other types of information stored in databases comprising large amounts of sensitive data that is being updated frequently, for example and without limitation financial and legal data. By using a batch table for data filtering and a snapshot table for data retrieval, the system's performance remains substantially predictable and stable regardless of the base tables' size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawing making apparent to those skilled in the art how the several forms of the invention may be embodied in practice. In discussion of the various figures described herein below, like numbers refer to like parts. The drawings are generally not to scale.

In the accompanying drawings.

DETAILED DESCRIPTION OF THE INVENTION

Before at least one embodiment of the invention is explained in detail, it is to be understood that the invention is not necessarily limited in its application to the details set forth in the following description or exemplified by the Examples. The invention is capable of other embodiments or of being practiced or carried out in various ways.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawing.

Various embodiments of a system and method for analysis, archiving, retrieval and display of medical diagnostics related data are disclosed hereinbelow.

Figure 1:
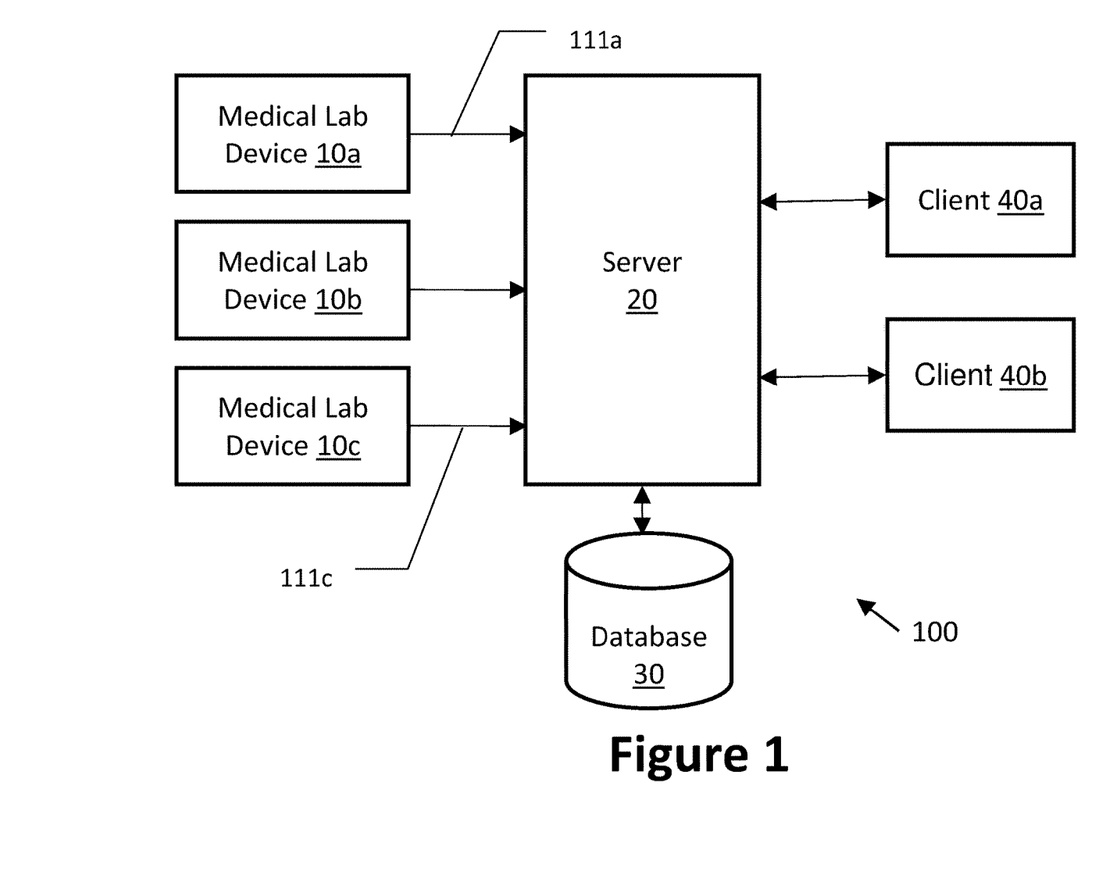
FIG. 1 schematically illustrates a typical physical environment of the medical diagnostics system.

Reference is now made to FIG. 1 schematically illustrating a typical physical environment of the medical diagnostics system embodiment 100. In this embodiment, system 100 comprises three medical lab devices 10a, 10B and 10C, a server 20, a database serving as a data storage unit 30 and two clients 40a and 40B. However, it should be noted that number of components may be different or larger. Devices 10 may be operated automatically or by an operator such as a physician or a technician. Devices 10 are capable of running medical processes, for example and without limitation: perform examinations to patients or to perform laboratory examinations on biological sample. For example, Devices 10 may conduct chromatography or spectroscopic tests on blood or urine samples taken from patients, etc. Devices 10 are also configured to produce diagnostic data records 111 related to the medical process. Diagnostic data records are sent to at least one server 20, and stored in at least one data storage unit 30. Optionally or additionally backup devices for database 30 (not seen in these figures) may be used.

Diagnostic data records typically accumulate such that patients' overall data stored in the data storage unit may comprise information such as but not limited to:

1. Patient personal & contact information: unique ID, sex, age, marital status, address, phone, insurance company, financial balance, etc.

2. Patient medical information: medical background, diagnosed diseases, visits to medical care facilities, previous lab results, etc.

3. Diagnostic device information: device ID, operator ID, etc.

4. Specific sample information: time and date records of sample gathering, time and date of sample analysis by the medical device, medical device measured raw or processed data, analysis results, etc.

Diagnostic data records are periodically produced by physical medical devices 10. Time intervals between subsequent diagnostic data records creation are generally predictable, and bound by measureable parameters such as but not limited to the number of medical devices producing the data records. Smart arrangement of diagnostic data records in the data storage unit during the record insertion process facilitates efficient retrieval of relevant data for substantially real time diagnostic data displays.

Figure 2:
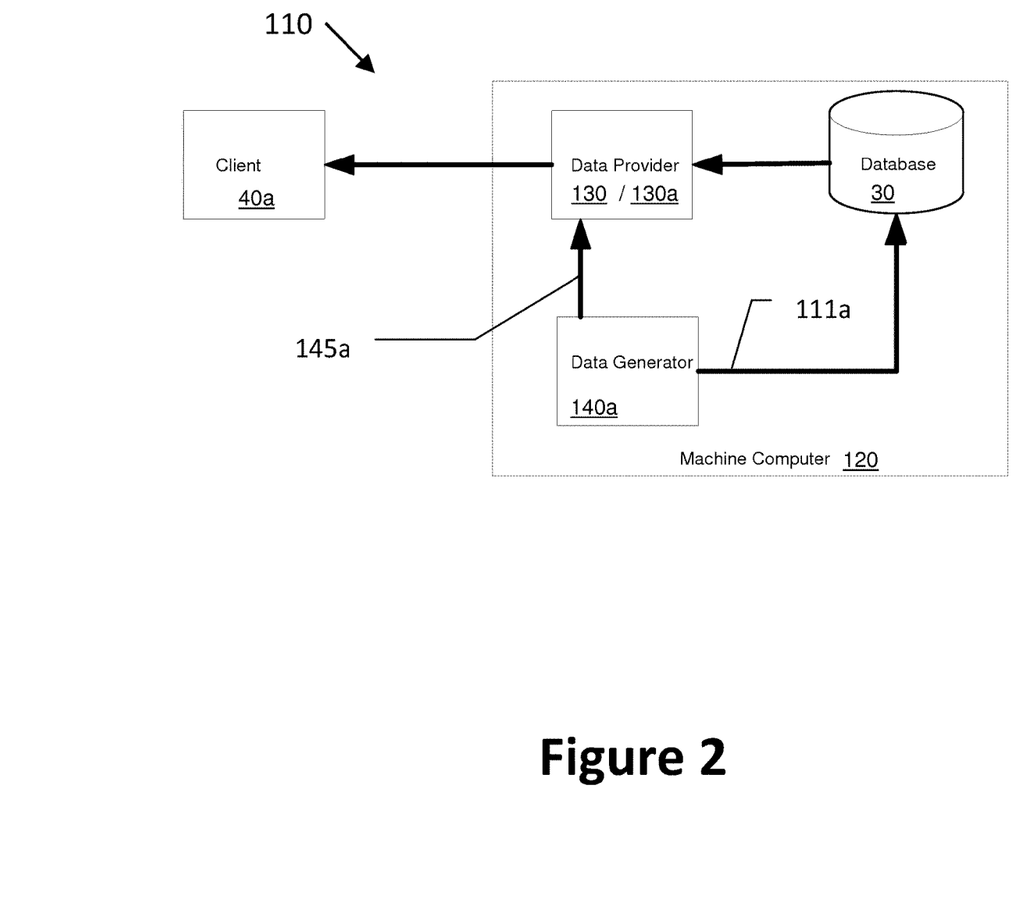
FIG. 2 schematically depicts a simplified block diagram showing the interaction of a client with a machine computer.

In some embodiments, specifically when a single device 10 is used, a machine computer 120 associated with said device may assume the functionality of the server 20. However, even when one device 10 is used, a plurality of processors or processes within the device may generate data records 111 and are thus termed data generators 140. The Data Generator generates records of data such as results, orders, logs and the likes. This situation is illustrated in FIG. 2. In other embodiments, (for example, but not limited to) where a plurality of devices 10 interacts with one or a plurality of clients 40, data generators 140 are located in the devices 10, while other computing functions, such as data provider 130 and database 30 are located in server 20. Thus, the functions of machine computer 120 may encompass the functionality of server 20.

A user interacts with the system using a viewing unit represented by the client 40. For the purpose of this discussion, the term "Client 40" refers to the UI (User Interface component). The viewing may be done using a computer such as a PC, a terminal or a mobile device and may be situated in proximity to server 20 or remotely. Generally, the client 40 has at least a display such as a screen and input devices such as keyboard and a mouse. The client has a limited processing power and limited data storage capacity, usually the processing and storage capabilities of the client are substantially less than the corresponding capabilities of the server.

FIG. 2 schematically depicts a simplify block diagram 110 showing the interaction of a client 40 with a machine computer 120.

For drawing clarity, only one data generator 140 (namely 140a) and one client 40 (namely 40a) are seen. Data provider 130 is used for transferring needed data from database 30 to client 40a.

When a new data 111a is generated by the data generator 140a, it is added to database 30. Concurrently, data generator 140a issues a "new data notification" 145a to notifies the data provider 130 which transfers that new data to the client 40a.

It should be noted that there can be several clients 40 and several Data generators 140, but only one Database 30. Preferably there is one Data Provider 130 serving all clients 40, however in some embodiments each client 40 is served by a dedicated data provider 130. The client (or clients) 40 may be either local (executed on the same computer with the DB 30) or remote (running from a remote computer).

The Data Provider 130 provides the data to the client 40. The Data Provider enables the client to run on a remote or a local computer seamlessly. It also acts as a buffer between the Client and the Database.

Figure 3:
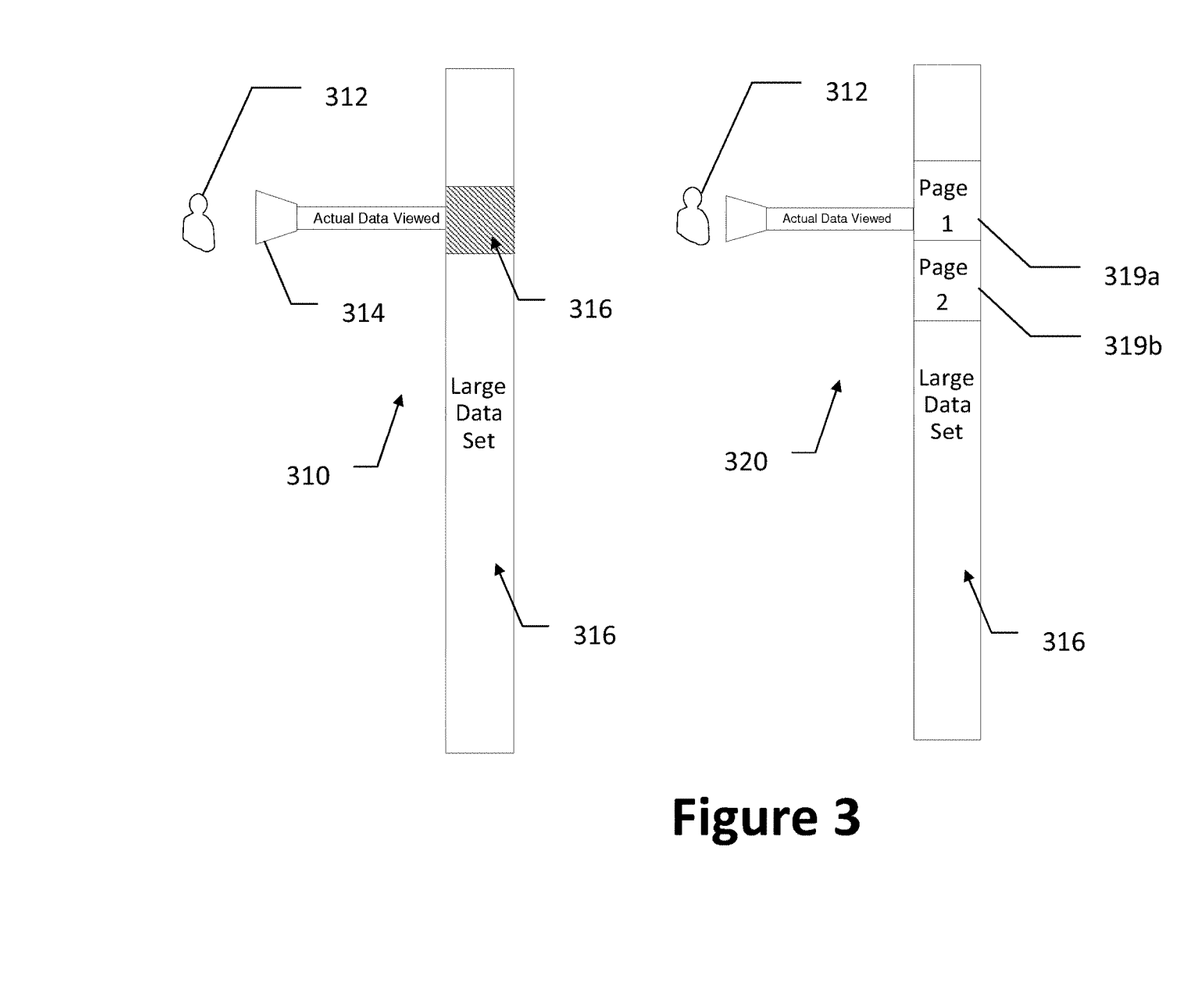
FIG. 3 schematically shows the concept of paging used for viewing data by the user at client.

FIG. 3 schematically shows the concept of paging used for viewing data by the user at client 40.

As can be seen in illustration 310, at any given time, a user 312 views, using the client 40 display, a view 314 with a small amount 316 of the data out of the large data 318 in database 30. The user may choose to display information selected from the large database 30 by defining criteria for filtering and/or sorting the information. Getting all the Data from the database 30 to the client 40 would result in: Very large communication block sent through the communication channels; and a necessity to store and sort the large amount of data at the client's side. This poses high burden on the speed of the communication channels, the storage capacity at the client and the clients processing power and speed, thus increasing the system cost.

The filtering and/or sorting may be performed according to embodiments of the present invention by optimized search tables that may be customized to match the client's search/view criteria, wherein the search tables may be updated in real time.

The Paging Mechanism seen in illustration 320 is capable of managing data transfer from the database 30 to a client 40 in an optimized way.

The paging mechanism is combined of two complementary phases: Server side paging and Client side paging.

The Server side paging mechanism comprises interfaces for creating a list of results according to the criteria given by the user; and interfaces for navigating over the generated list of results by providing the list ID and the range of requested results. The interfaces are accessed via server side components hosted on the WAS (Data Providers) and the actual list of results is stored optimally in the database. The result object that returns to the client when creating a list of results includes the created list ID and the number of results in the list.

The client side of the paging mechanism is done by determining a page size and requesting the server to transfer chunks of data. Each chunk size is a page size such as page 1 or page 2 (319a, 319b and 319c respectively, but number of pages may be larger or there may be only one page associated with a specific criteria). The client requests only for the needed pages and not for all the data (which may be very large).

Using the paging method, the client loads load only the relevant portion of the data needed for viewing. When the user changes the view position, loading of new data as required.

In some embodiments, when two or several pages are associated with viewing criteria, the client may request, obtain and pre-load into a local storage at least one, and optionally few of the next pages to be viewed according to the sorting and viewing criteria. Next-page pre-loading enables rapid scrolling or page-switching with only modest increase of the client local storage capacity. Pre-loading make uses of the time the user spends reviewing the current page to pre-load the next anticipated view. Obviously, if the user chooses to change the filtering or sorting criteria and review different type of data, the pre-loading actions were wasted. Thus, pre-loading imposes some burden on the communication channels.

After reviewing the displayed data, the user may want to view other portion of the data associated with the same filtering and sorting criteria by: scrolling or by Jumping to a new location (random access), for example by using the slider.

Using pages larger than the actual display may prevent delays when scrolling (as long as the scrolling is within the loaded page). Pre-loading the adjacent pages may also prevent delays when scrolling.

However, jumping to a new location may cause a delay until the new data is fetched. Using smaller page size may decrease this delay. The page size is thus optimized: not too large—to avoid a fetch delay in a single call to the DB, and not too small because if the page size is too small many requests will be issued to the DB when the user scrolls down.

Figure 4:
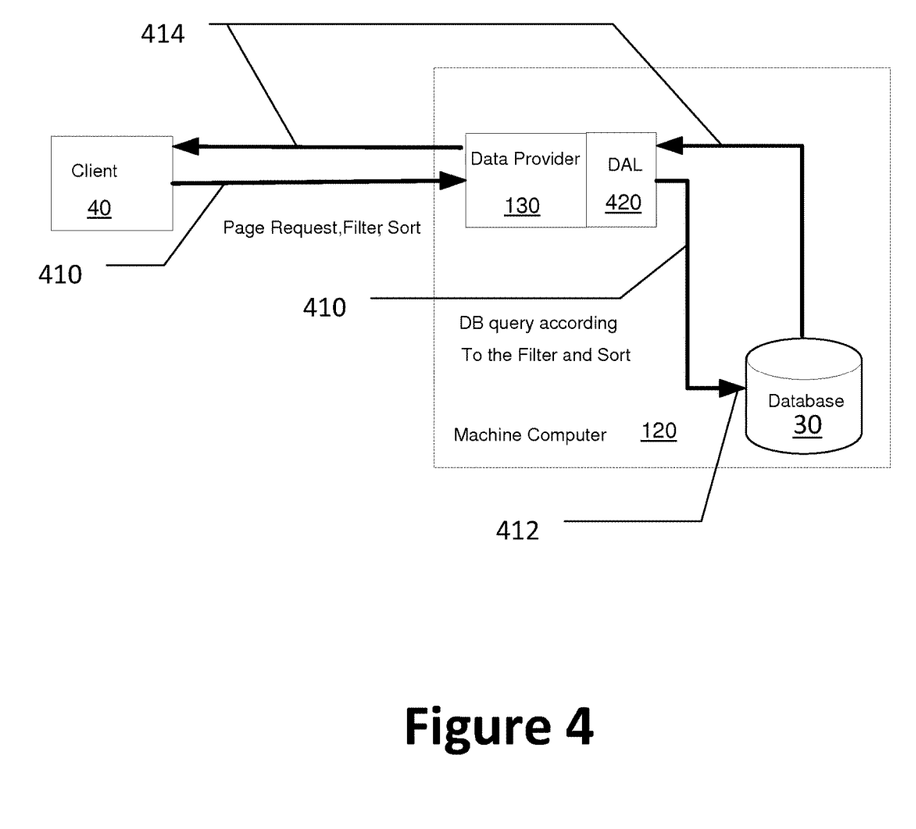
FIG. 4 schematically depicts the process of transferring requested data from the database to the client.

FIG. 4 schematically depicts the process of transferring requested data from the database 30 to the client 40. For drawing clarity, only one client is seen, and the data generator and data insertion into the database were omitted from the drawing.

The user may request to view a subset of the data records by specifying a filter to narrow the number of data records to view. Additionally, the user may want to view the data in a specific order or arrangement using defined sorting criteria. The filter and the sort type are specific to each implementation and user. Generally, a plurality of filtering and sorting combinations may be defined by the users. According to some embodiments of the present invention, the filtering and/or sorting may be performed by optimized search tables that may be customized to match the client's search/view criteria, wherein the search tables may be updated in real time.

When a user choose to change the display on his client, he selects a new filter and/or sort combination.

The user's client 40 sends a page request 410 to the data provider 130 which interfaces with the database 30 via the Data Access Layer (420). The DAL 420 provides interface for accessing the database via an assembly reference. It provides the interface for creating a generic list of results represented by the returned list ID, and the interfaces for navigating a results list by list ID and range. The DAL 420 exposes database's common data objects in its interfaces to the Data Provider 130 (or data providers 130a, b, etc., if dedicated data providers are used with each client), and it is charge of converting them to the DB types exposed in the matching DB stored procedures.

The Data Provider 130 (or data providers 130a, 130b, etc.) are the server side components, hosted on the server 20 or the machine computer 120, which serve as the client's façade to the database 20 for interactions related to paging. Optionally, the data provider comprises a Results Provider which implements the paging mechanism for fetching results.

The clients (40a, 40b, etc.) send the user's search and sorting criteria along with its client unique ID to the appropriate data provider and gets a unique list ID for that identifies the created list of results in the database. The client then communicate with the data provider and uses the given list ID to navigate over the results list, by defining the range of expected results (start and end index of requested results within the list).

The Data Access Layer (DAL) 420 (DALs 420a, 420b, etc.) provides interface for accessing the database via an assembly reference. It provides the interface for creating a generic list of results represented by the returned list ID, and the interfaces for navigating a results list by list ID and range. The DAL exposes the database's common data objects in its interfaces to the Data Providers, and it is charge of converting them to the DB types, exposed in the matching DB stored procedures.

The DB is requested 412 to bring specific pages according to the defined filter and sort and thus the filtering and the sorting may be done by specifying an appropriate query 412 to the DB 30 that will be implemented in the DAL 420. In each page request the client sends the filter and the sort type along with the page request. Note that each filter and sort change requires the client to reload its data.

Database 30 provides the data 414 to client 40 via DAL 420 and data provider 130.

The client loads the new data by loading the current page and swapping out all other pages in its memory.

Figure 5:
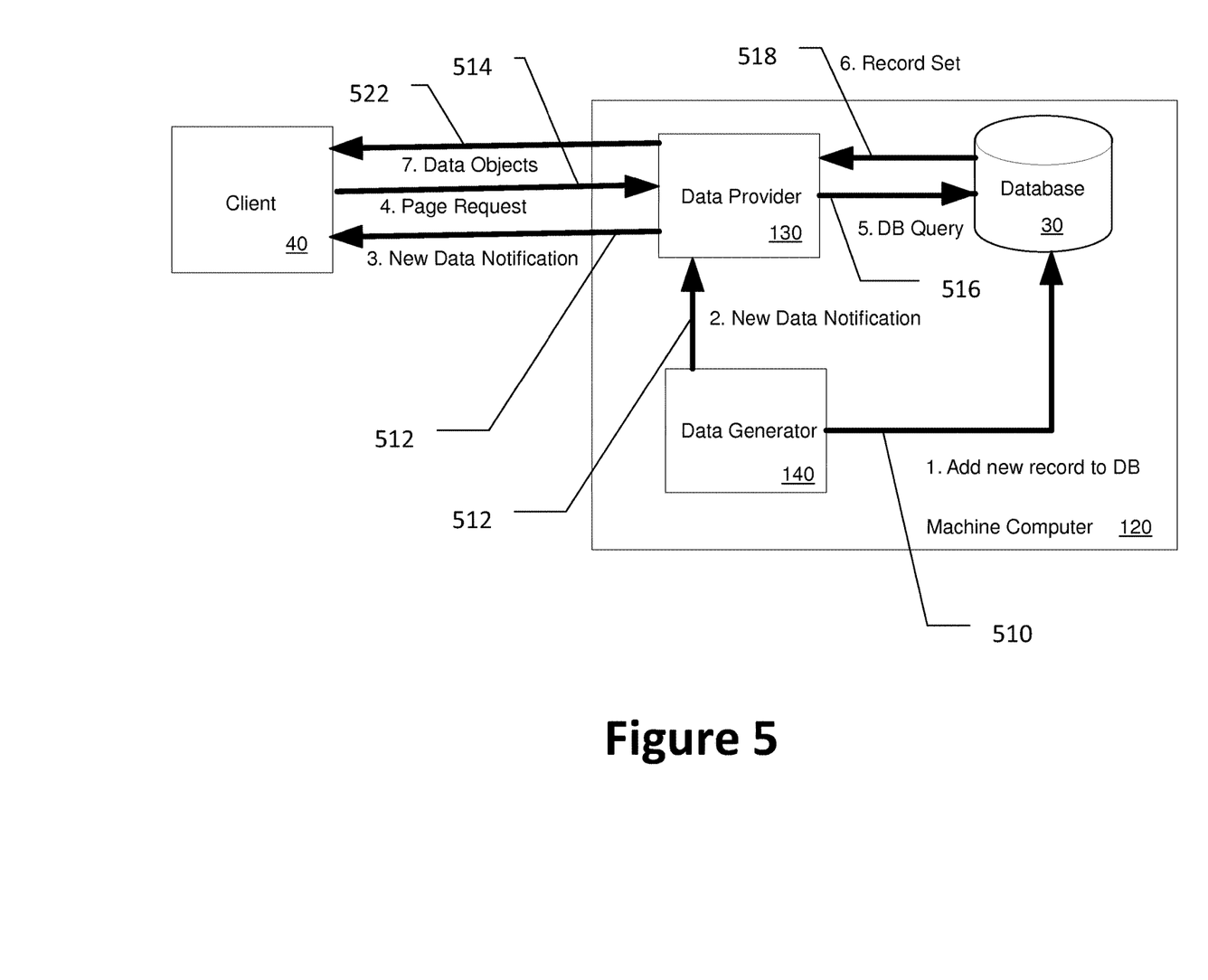
FIG. 5 schematically depicts a method of inserting a new data into the database while concurrently updating the client's page, provided that the new data is associated with the page currently viewed by the user.

FIG. 5 schematically depicts a method of inserting a new data into the database while concurrently updating the client's page, provided that the new data is associated with the page currently viewed by the user.

Some embodiments of the present invention may provide smart insertion, arrangement, and processing of a new result introduced to the system. A new data record may be validated against various filters applied by clients of the system, and an appropriate notification may be sent to the relevant clients.

When new records are generated by one of the data generators 140 while at least one client 40 is active, the new data 510 is inserted to the DB 30.

Preferably, the new data 510 is to be reflected in client's view as soon as possible. However, if the client is looking at a part of the view which does not contain these new records, no updating is needed at the client. Since the client page is updated by a page request 410 as seen in FIG. 4, client has no way of knowing to which page this new record was entered. It would be a high burden on the system to reload the current page every time a new record had been entered, as reloading current page is similar to the operation which is needed for a filter change or a sort change.

A method for updating and displaying medical diagnostics data according to embodiments of the present invention may include generating by at least one data generator a data record and a data notification associated with the generated data record and inserting the generated data record to a database.

For example, the following process may used to ensure efficient and fast page update:

1. When a new record is generated by the data generator 140 and is inserted into the database 30 in its proper place.
2. The data generator 140 further issues a new data notification 512 to data provider 130.

Additionally, the method may include applying to the data notification at least one client filter associated with at least one client. For example, the following steps may take place:

3. The new data notification 512 is passed to the client 40 via the data provider 130. Optionally, the new data notification does not include the entire information in the new record, but only enough information that enables the system to determine if the new record meets the criteria of the current filter, and optionally to sort the new record and to determine if the new record is included in the current page or the current user's view.
4. Client 40 examines the new data notification, and only if it determine that the new record is needed at the client (that is—the new record is associated with the current viewed page), it issues a page request 514 to the data provider 130. Optionally, Data provider 130 performs the examination of the new data notification, and only if it determine that the new record is needed at the client it sends the notification to the client 40.

Upon determination that the data notification matches the client filter, the method may further include generating and submitting a database query to the database by a data provider. The database may provide to the data provider, in response to the query, a record set associated with an updated view including the generated data record. The data generator may submit to the at least one client data objects associated with the record set. The at least one client may display the updated view comprising information derived from the record set.

For example, the following steps may take place:

5. Page request 514 prompts the data provider 130 to issue a database query 516 to database 30.
6. Database query 516 prompts data base 30 to send a record set 518 to data provider 130.
7. Data objects 522 associated with the current page (already updated with the new record 510) is sent by the data provider to the client that uses the updated page to update its view.

In some embodiments of the present invention, the applying of the at least one client filter is performed by the data provider. In other embodiments, the applying of a client filter is performed by the at least one client, the applying further includes: submitting the data notification, by the data provider to the at least one client; applying to the data notification by the at least one client a respective filter associated with the at least one client. In such cases, the generating of a database query may include, upon determination that the data notification matches the client filter, generating and submitting a page request by the at least one client to the data provider; and generating by the data provider a database query associated with the page request.

According to some embodiments of the present invention, the at least one client may be one of a plurality of clients, and/or the at least one data generator may be one of a plurality of data generators.

Optionally, if page pre-loading is used (as depicted above), when the new record is associated with a page or pages pre-loaded at the client (even if that pre-loaded page is not currently viewed by the user), a similar process occurs such that the pre-loaded page (or pages) are re-loaded such that updated copies are present at the client.

Optionally, a mechanism which enforces a minimum time between updates may be implemented in the client. This mechanism delays the request for new data if data is entered at a high rate to prevent overloading the system and/or to reduce view flickering.

In some exemplary embodiments the client side is implemented by using a WPF (WebSphere Partition Facility, an IBM facility) DataGrid which supports data virtualization and, by binding the DataGrid to a special class which implements the IList interface and the actual paging. Data virtualization in the DatGrid is supported by specifying special virtualizing attributes.

The class which supports the Paging is AsyncVirtualizingCollection<T>. This class uses generics to support paging of any data type. It supports both synchronous and asynchronous paging. Synchronous paging means that when there is a page request the client waits for the page to be loaded and only then retrieves the item requested. Asynchronous paging means that when the application requests an item and the page is not loaded—a dummy item is retrieved and later when the page is actually loaded the real item is updated in the client.

It should be noted that a possible disadvantage of synchronous paging is that it may cause the client to freeze if the data request takes a lot of time. On the other hand, a possible disadvantage of asynchronous paging is that it may causes flickering in the client because of displaying the dummy item and then the real item. This problem is mitigated by choosing a reasonable page size.

Both the synchronous and the Asynchronous options may be implemented in the client. It was found that in the current application, the synchronous option performs well and looks better.

The AsyncVirtualizingCollection gets an IItemsProvider<T> in its constructor. The ItemsProvider is a class which knows how to retrieve elements of the specified types. The ItemsProvider may be implemented for each data type which we need paging for. The ItemsProvider operates by simply calling the Model and getting the items according to the range specified.

The AsyncVirtualizingCollection supports the IVitrualCollectionInfo interface. This interface gives data about the paging state of the collection and it is used to debug the paging mechanism.

Figure 6:
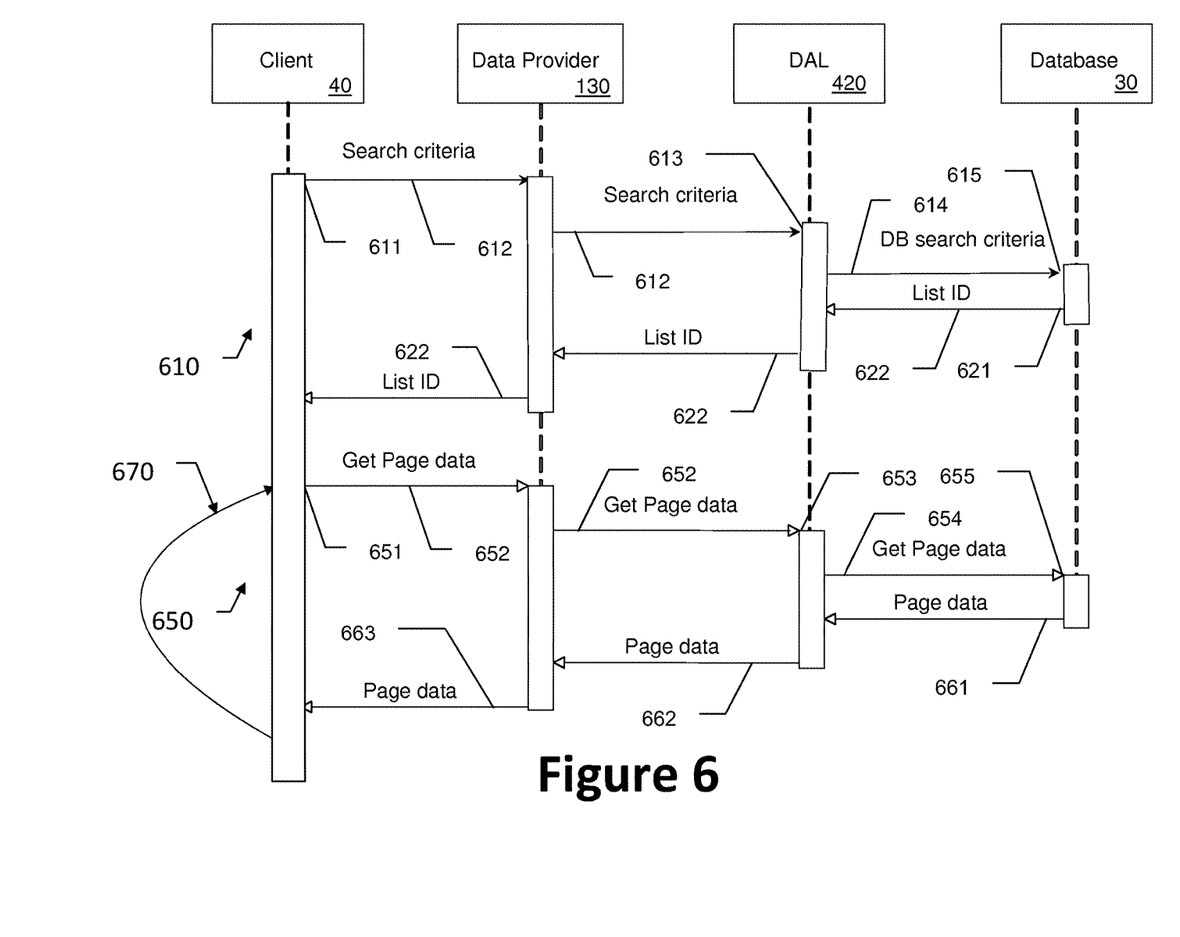
FIG. 6 shows some details of a page-loading and navigation process.

FIG. 6 shows some details of page-loading and navigation process, e.g. a method of fetching, navigating within, and displaying a part of large medical diagnostics dataset according to embodiments of the present invention.

The paging mechanism is combined of the two following steps: Creating a list of results, and Navigating over a list of results.

A. Creating a List of Results

This process describes the process of creating a list of matching results 610 according to the client specification:

1. The method may include receiving from a client, by a data provider at a server, selected search criteria. For example, the client 40 invokes 611 a "create list" interface on the appropriate data provider with a filter and sorting criteria. The search criteria are sent 612 to the data provider 130.
2. The method may include submitting the search criteria to a Data Access Layer (DAL). For example, the data provider 130 sends the search criteria to the DAL 420.
3. The method may include converting by the DAL the search criteria to database type search criteria and sending the database type search criteria to a database. For example, the DAL 420 converts 613 the search criteria 612 to DB types 614 and calls the matching stored procedure 615.

The method may include creating a list of matching results in a temporary table in the database and returning a list identifier of the list to the client. For example, the following steps may take place:

4. List of matching results is created 621 in a temporary table in the database and the "list ID" 622 that identifies this list is returned to DAL 420.
5. The DAL 420 returns a list ID 622 that identifies the generated database list of results to the data provider 130.
6. The Data Provider 130 returns the list ID 622 to the client 40.

After receiving the list of results the client can navigate over the generated list as follows:

B. Navigating Over a List of Results

This process 650 describes the process of getting the appropriate data from the database to display/facilitate at the client side:

1. The method may include receiving, by a data provider at a server, a page request including a list identifier of the created list and a page range. For example, the client 40 invokes a fetch page data interface 651, sending the appropriate data provider 130 a request (Get Page data, or page fetch criteria) 652 with a list ID and a page range (start and end index).

The method may include converting by the DAL the page request to a database type page request and sending the database type page request to the database. For example, the following steps may take place:

2. The data provider 130 sends the page fetch criteria 652 to the DAL 420. Accordingly, the method may include submitting the page request to the DAL
3. The DAL 420 converts 653 the Get Page data 652 to DB types 654 and calls the matching stored procedure 655.

The method may include creating a page size list of results matching the page request and returning the page size list of results to the client. For example, the following steps may take place:

4. The database 30 returns a page size list of results 661 to the DAL 420.
5. The DAL 420 returns a list 662 of the DB requested data objects defined in the fetch interface.
6. The Data Provider 130 returns the list of data objects 663 to the client 40.

According to some embodiments of the present invention, the method may further include displaying the page size list of results.

In some embodiments of a method according to embodiments of the present invention, the selected search criteria may include a selected filter and selected sort criteria. The creating of a list of results may be repeated, for example, by receiving from a client, by a data provider at a server, different selected search criteria, comprising the selected filter and different sort criteria. The navigating over a list of results may be repeated, for example, by receiving, by a data provider at a server, a page request including a list identifier of the created list and a different page range Accordingly, to navigate 670 within the same search criteria, the same process B 650 is repeated for any additional paging requests using the same list ID and a different page range. The client uses the "results fetch criteria" to navigate over the list of results, thus this object includes the list ID and the results range (min and max index)

When the sort criteria are changed, process A 610 is repeated.

Figure 7:
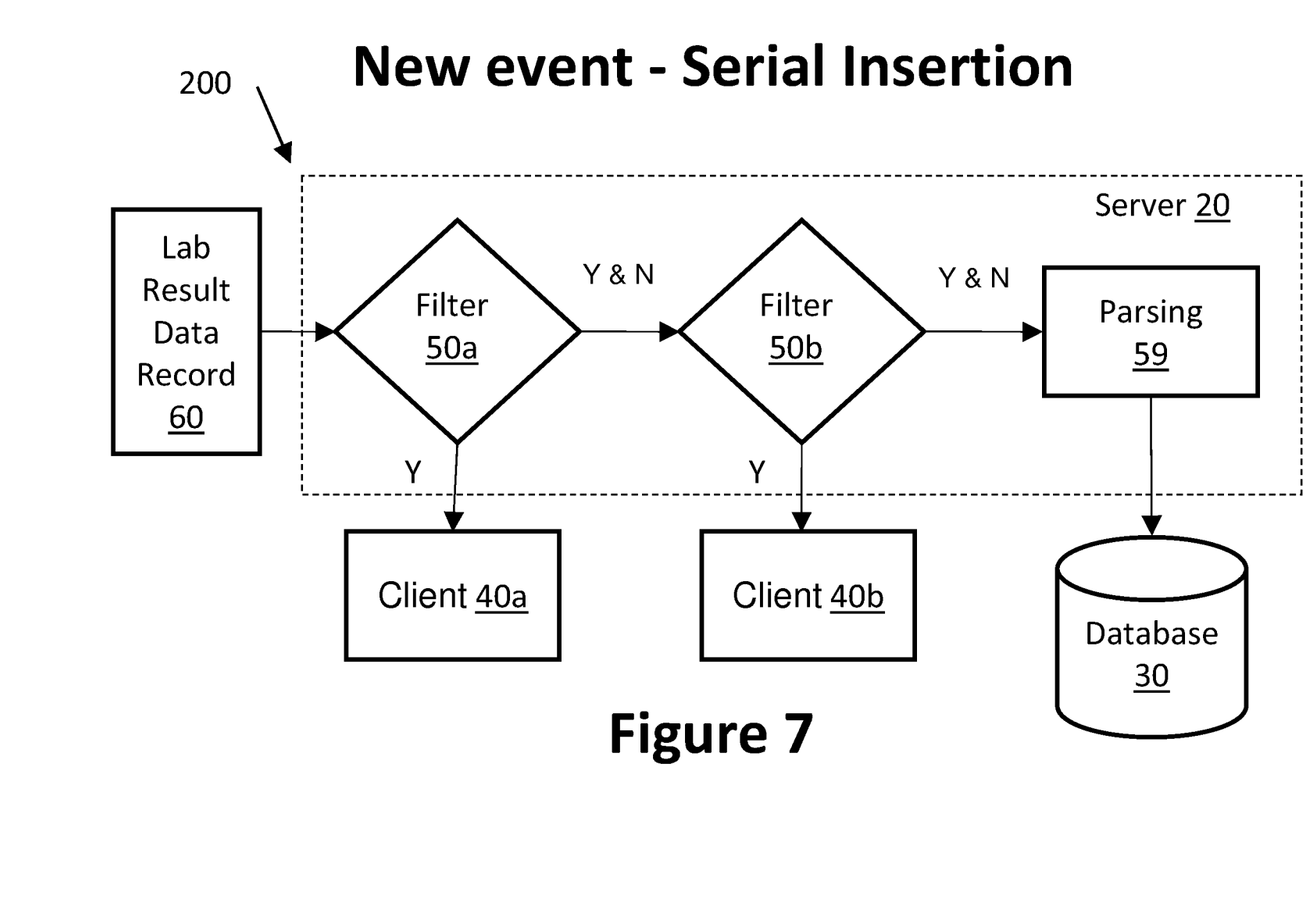
FIG. 7 is a schematic data flow of serial data insertion into a data storage unit.
Figure 8:
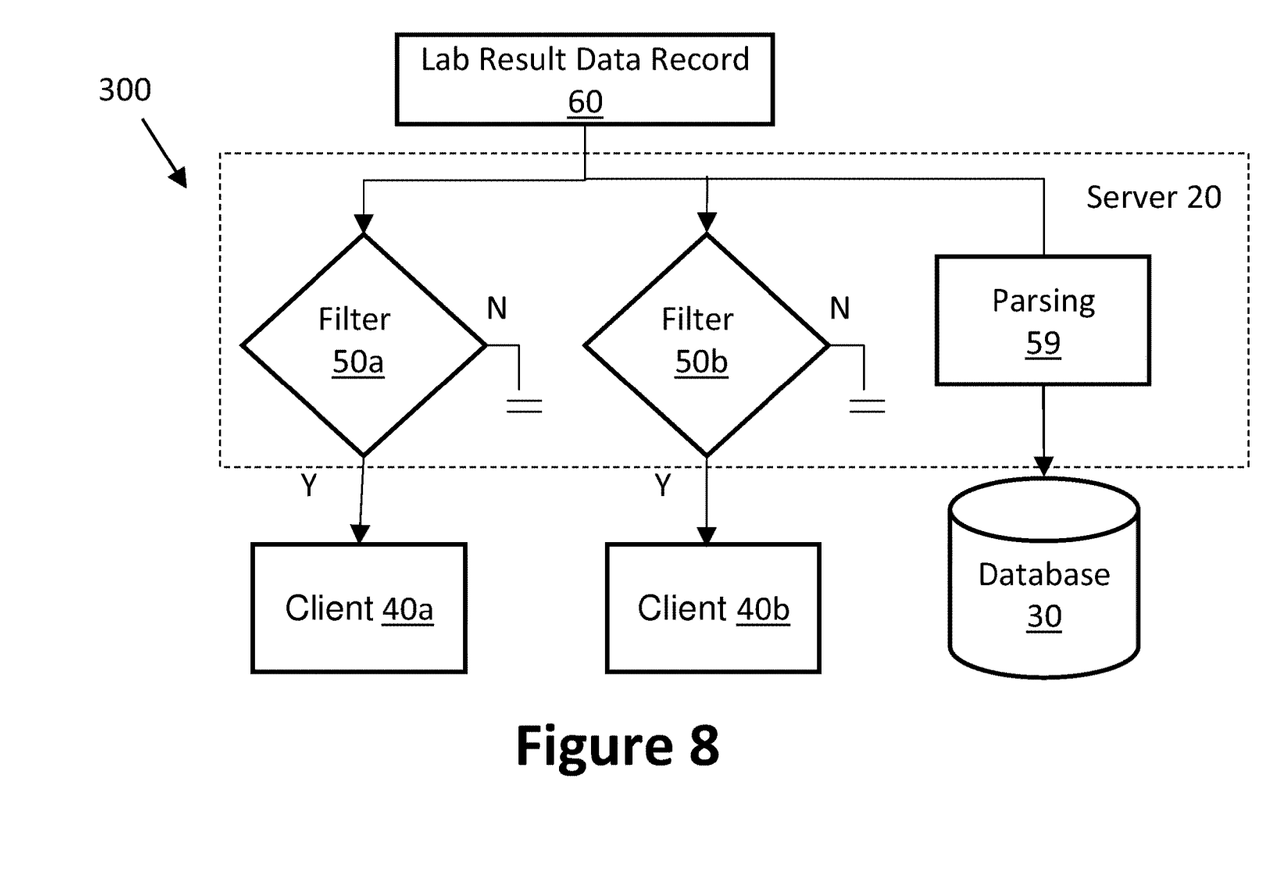
FIG. 8 is a schematic data flow of data insertion into a data storage unit wherein the data is first parsed before it is inserted into a database.
Figure 9:
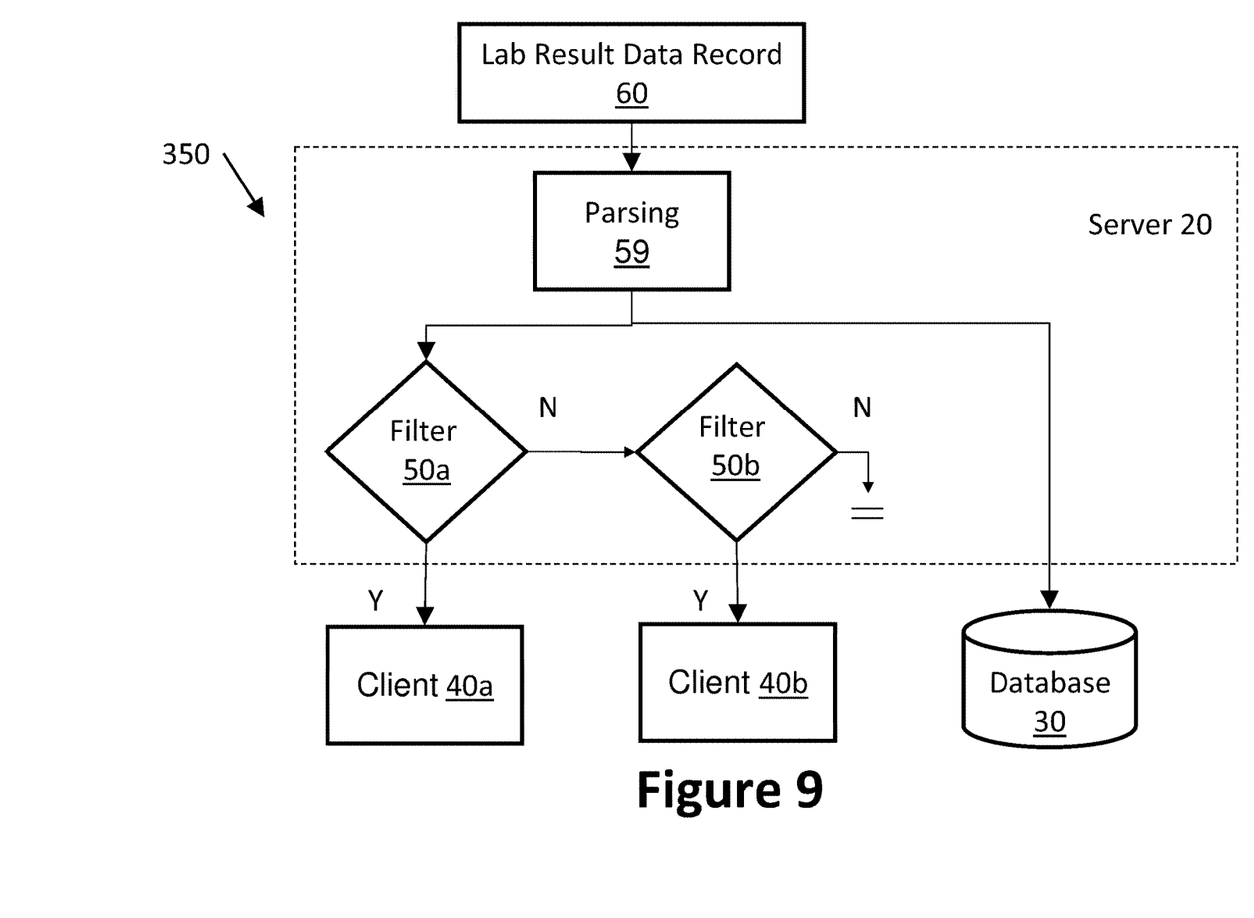
FIG. 9 is a schematic data flow of data insertion into a data storage unit, wherein the data is first parsed before it is inserted into a database and concurrently filtered, first by a first filter and then by a second filter.

FIGS. 7, 8 and 9 illustrate serial and parallel data insertion processes 200, 300 and 350 respectively, utilized by system 100 in FIG. 1. Data insertion and management as described herein enables real-time update of clients' display as well as quick, effective retrieval of diagnostic data records by clients 40a and 40b, such that they are able to create a substantially real-time view of diagnostic data received from medical lab devices 10. Additionally, Data insertion and management as described herein enables real-time parsing of the data 60 arriving from medical lab devices 10 such that it is stored in database 30 in a format that enables fast and efficient retrieval by clients 40.

Clients 40 (for drawing clarity only two clients, 40a and 40b are seen in these figures, but number of clients is generally larger) are connected to server 20. Each client 40 is a workstation such as a PC, a terminal or a viewing station comprising at least a user interface and a display such as a screen. The data seen on the screen is determined by the user by defining a view, which can be characterized by filters 50a and 50b respectively. For example, client 40a may be used by a device technician to view sample results diagnosed by a specific device, and client 40b may be used by a physician to view lab results for a specific patient. Client 40a will define a filter 50a relating to the medical device, and client 40b will define a filter 50b relating to the patient. For example, filters 50a and 50b may be or may be executed by optimized search tables that may be customized to match the client's search/view criteria, wherein the search tables may be updated in real time.

The client sends a filter definition to the server, and a relevant data query is executed on the data storage unit (30 in FIG. 1) to retrieve relevant data which exists in the database. A record list pertaining to the filter is created within the database, such that the record list is associated with a unique ID which will be referred to herein as a "List ID". The record list may be a duplication of the data, or a hash table which points to relevant data in the database. The record list may contain complete records or records containing selective data, according to the filter definition. The list ID is sent to the client, and is used to retrieve the relevant data which will be presented in the client view.

When a new data record 60 is to be inserted into the data storage unit 30, the system first checks the new record against filters 50a and 50b. Checking against multiple filters for multiple views can be done either serially (FIG. 7) or in parallel (FIG. 8). If matched against one or more of the filters, a relevant record list is updated, and a notification with the new data is sent to the client view, thus enabling data to be updated in data snapshot for the client view immediately as new data arrives. The transparent snapshot update eliminates the need to re-fresh the client view. This optional workflow solves the new data update issues. It moves the burden from the UI that needs to pull the data from the server, to the server that needs to push the data to the appropriate clients.

In FIG. 9, the data is first parsed before it is inserted into database 30 and concurrently filtered, first by filter 50a and then by filter 50b.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

In the claims, the word "comprise", and variations thereof such as "comprises", "comprising" and the like indicate that the components listed are included, but not generally to the exclusion of other components.

Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The scope of the present invention is defined by the appended claims and includes both combinations and sub combinations of the various features described hereinabove as well as variations and modifications thereof, which would occur to persons skilled in the art upon reading the foregoing description.

The invention claimed is:

1. A method for smart insertion of new medical diagnostics data into a database for client devices displaying current views of the database, the method comprising:
    acquiring, by at least one medical instrument, medical diagnostic data;
    generating a data record from the medical diagnostic data; and
    performing a smart insertion operation to update the database, the smart insertion operation updating, substantially in real time, views of the database displayed in user interfaces of client devices that are impacted by the generated data record, the smart insertion operation comprising:
        inserting the generated record into the database;
        generating a notification that indicates the insertion of the generated data record into the database;
        determining, for each of a plurality of client devices, whether a current page view of the database that is currently displayed in a user interface of the client device would change due to the insertion of the generated data record into the database if the current view were updated, wherein, for a given client device, the determining includes:
            identifying a current filter that was applied to generate the current page view of the database that is currently displayed in the user interface of the given client device; and
            applying the current filter to the notification to determine whether the generated data record will result in a change to the current page of the view of the database that is currently displayed in the user interface of the given client device if the current view were updated; and
        providing, to those of the client devices for which the current page view would change due to the insertion of the generated data record into the database if the current view were updated, an updated page view including information derived from the generated data record, wherein providing the updated page view for a given client device includes:
            generating and submitting a database query to the database by a server, the query configured to request a record set for updating the current page view displayed in the user interface of the given client device;
            providing, by the database in response to the query, the record set for updating the current page view displayed in the user interface of the given client device, the record set including the generated data record; and
            providing, for display in the user interface of the given client device, an updated page view comprising information derived from the record set including the generated data record, the updated page view provided substantially in real-time relative to the acquiring of the medical diagnostic data.

2. The method of claim 1, wherein the current filter for a given client device of the plurality of client devices is applied to the notification by the server.

3. The method of claim 1, wherein applying the current filter for a given client device of the plurality of client devices to the notification comprises:
    submitting the notification to the given client device; and
    receiving, from the given client device, a page request associated with the notification,
    wherein the database query is based on the received page request.

4. The method of claim 1, wherein applying the current filter for a given client device of the plurality of client devices to the notification comprises:
    sending the notification to the given client device; and
    receiving an indication from the given client device that the generated data record corresponds to the current page of the view currently displayed in the user interface of the given client device.

5. The method of claim 1, wherein the at least one medical instrument is one of a plurality of medical instruments.

6. The method of claim 1, further comprising:
after providing the updated page to a given client device of the plurality of client devices, preloading a second page by providing, for display in the user interface of the given client device, the second page, the second page being one that is anticipated to be displayed after the updated page.

7. The method of claim 6, wherein the second page immediately follows the updated page.

8. The method of claim 6, wherein the updated page has a size that is larger than a size of a display of the given client device.

9. The method of claim 6, further comprising, for a given client device of the plurality of client devices:
determining an amount of time since a previous update to the current page of the view currently displayed at the given client device; and
comparing the amount of time to a minimum time, wherein providing the updated page to the given client device is delayed if the amount of time equals or exceeds the minimum time.

10. The method of claim 1, further comprising, for a given client device of the plurality of client devices:
receiving a filter definition of the current filter from the given client device;
creating a record list based on the filter, the record list having a unique identifier; and
sending the unique identifier to the given client device, wherein the given client device uses the unique identifier to retrieve data from the database that passes the filter for incorporation into the current page view.

11. The method of claim 10, wherein the record list includes a copy of at least some of the data that passes the filter.

12. The method of claim 10, wherein the record list includes pointers to at least some of the data that passes the filter.

13. A system for displaying medical diagnostics data and smart insertion of new medical diagnostic data for client devices displaying current views of the medical diagnostic data, the system comprising:
a database storing a corpus of medical diagnostic data;
at least one medical instrument configured to acquire medical diagnostic data;
a plurality of client devices, each client device configured to display user-defined views of the corpus of medical diagnostic data; and
a data provider configured to:
receive new medical diagnostic data from the at least one medical instrument;
add the new medical diagnostic data to the corpus; and
perform a smart insertion operation to update the database, the smart insertion operation updating, substantially in real time, views of the database displayed in user interfaces of client devices that are impacted by the generated data record, wherein being configured to perform the smart insertion operation includes being configured to:
generate a notification responsive to receiving the new medical diagnostic data;
determine, for each of the plurality of client devices, whether a current page view of the database that is currently displayed in a user interface of the client device would change due to the insertion of the generated data record into the database if the current view were updated, wherein, for a given client device, wherein being configured to determine whether the current page view of a given client device would change due to the insertion of the generated data record includes being configured to:
identify a current filter that was applied to generate the current page view of the database that is currently displayed in the user interface of the given client device; and
apply the current filter to the notification to determine whether the generated data record will result in a change to the current page of the view of the database that is currently displayed in the user interface of the given client device if the current view were updated; and
provide, to those of the client devices for which the current page view would change due to the insertion of the generated data record into the database if the current view were updated, an updated page view including information derived from the generated data record, wherein being configured to provide the updated page view for a given client device includes being configured to:
generate and submit a database query to the database, the query configured to request a record set for updating the current page view displayed in the user interface of the given client device;
provide, by the database in response to the query, the record set for updating the current page view displayed in the user interface of the given client device, the record set including the generated data record; and
provide, for display in the user interface of the given client device, an updated page view comprising information derived from the record set including the generated data record, the updated page view provided substantially in real-time relative to the new medical diagnostic data being added to the corpus.

14. The system of claim 13, wherein the data provider being configured to apply the current filter for a given client device of the plurality of client devices to the notification comprises the data provider being configured to:
send the notification to the given client device; and
determine that the current page view of the corpus currently displayed in the user interface of the given client device will change as a result of the addition of the new medical diagnostic data responsive to receiving an indication from the given client device.

15. The system of claim 13, wherein the data provider being configured to apply the current filter for a given client device of the plurality of client devices to the notification comprises the data provider being configured to:
submit the notification to the given client device; and
receive, from the given client device, a page request associated with the notification,
wherein the database query is based on the received page request.

16. The system of claim 13, wherein the data provider is further configured to:
preload a second page by providing, for display in the user interface of a given client device of the plurality of client devices, the second page, the second page being one that is anticipated to be displayed after the updated page.

17. The system of claim 16, wherein the updated page has a size that is larger than a size of a display of the given client device.

18. The system of claim 16, wherein the data provider is further configured to:
   determine an amount of time since a previous update to the current page of the view currently displayed at the given client device; and
   compare the amount of time to a minimum time, wherein providing the updated page to the given client device is delayed if the amount of time equals or exceeds the minimum time.

19. The system of claim 13, wherein the data provider is further configured to:
   receive, from a given client device of the plurality of client devices, a filter definition of the current filter for the given client device;
   create a record list based on the filter, the record list having a unique identifier; and
   send the unique identifier to the given client device, wherein the given client device uses the unique identifier to retrieve data from the database that passes the filter for incorporation into the current page view.

20. The system of claim 19, wherein the record list includes pointers to at least some of the data that passes the filter.

* * * * *